US005757011A

United States Patent [19]
Whitebook et al.

[11] Patent Number: 5,757,011
[45] Date of Patent: May 26, 1998

[54] X-RAY ONSET DETECTOR AND METHOD

[75] Inventors: Mark E. Whitebook, Dana Point; Paul P. Suni, Los Gatos; John R. Cover, Burbank, all of Calif.

[73] Assignees: Orbit Semiconductor, Inc., Sunnyvale; New Image Industries, Inc., Canoga Park, both of Calif.

[21] Appl. No.: 386,933

[22] Filed: Feb. 10, 1995

[51] Int. Cl.$^6$ .................................................. G01T 1/24
[52] U.S. Cl. ........................... 250/370.09; 250/370.08; 250/208.1
[58] Field of Search .................... 250/370.08, 370.09, 250/208.1; 378/98.8

[56] References Cited

U.S. PATENT DOCUMENTS

| | | | |
|---|---|---|---|
| 4,901,336 | 2/1990 | Nishiki | 378/98.8 |
| 4,905,265 | 2/1990 | Cox et al. | |
| 5,043,582 | 8/1991 | Cox et al. | |
| 5,149,455 | 9/1992 | Cox et al. | |
| 5,187,730 | 2/1993 | Fujihara | |
| 5,216,250 | 6/1993 | Pellegrino et al. | |
| 5,220,170 | 6/1993 | Cox et al. | |
| 5,252,509 | 10/1993 | Hosack | |
| 5,331,166 | 7/1994 | Yamamoto et al. | 250/370.09 X |

Primary Examiner—Edward J. Glick
Attorney, Agent, or Firm—Richard L. Myers

[57] ABSTRACT

An apparatus and method for visualizing a scene in the form of image rays projecting along a path includes a plurality of charge coupled device detectors disposed along the path to receive the image rays and to collect data. This data includes both noise data which is collected at a generally constant rate, and image data which is collected when the image rays are present along the path. A clock which facilitates discharge of the data from the image array has a first state wherein the data is retained in the detectors, and a second state wherein the data is discharged from the detectors. An event detector including a plurality of charge coupled device detectors forms an event array which places the clock in the first state when the image rays are present along the path and places the clock in the second state when the image rays are absent from the path. Accordingly, the noise data which combines with the image data in the image detectors is limited to that which accumulates while the image rays are present along the path.

16 Claims, 4 Drawing Sheets

X-RAY ONSET DETECTOR AND METHOD

BACKGROUND OF THE INVENTION

1. Field of the Invention

This invention relates generally to solid-state video imaging systems based on charge-coupled device (CCD) detectors, and more specifically to such systems which are adapted for use in X-ray imaging.

2. Discussion of the Prior Art

Solid-state video imaging systems based on charged-coupled device (CCD) detectors have become familiar in scientific applications, such as astronomical and space-based imaging systems, and commonplace in video-based consumer electronics, such as hand-held video cameras. In general, CCD detectors are used for visual-spectrum applications spanning wavelengths in a range of 400 nanometers to about 700 nanometers. Silicon-based CCDs have an even wider range of application extending from the near infrared spectrum to the ultraviolet spectrum.

More recently, the medical community has embraced CCD cameras for imaging applications, particularly in the endoscopy field where their small size and sensitivity is particularly appreciated. In a representative application, CCDs have been used in diagnostic X-ray imaging where the CCD detector takes the place of conventional film, and a computer-based image processing system with CRT display takes the place of a conventional viewing light-box. These CCD solid-state X-ray imaging systems offer the advantages of speed, sensitivity and convenient storage. In addition, they facilitate data transmission as well as image processing capability.

In general, CCD X-ray detection falls into two technical approaches, indirect and direct X-ray detection. Indirect detection is accomplished using a scintillator plate which emits visible photons in response to X-rays. These photons produce a visible light image which is then detected by a CCD detector.

In a direct X-ray detection process, the CCD detectors are positioned in the direct path of the X-rays. This system is closer in concept to that of the dental X-ray film technology where the film is exposed directly to the X-ray photons. There is no intervening scintillation plate to convert the X-ray image into visible light.

The indirect method offers the advantages of higher sensitivity and benefits from use of off-the-shelf CCD detector products. In addition, the X-ray opacity provided by the scintillator plate aids in shielding the CCD from the effects of direct X-ray radiation. By comparison, the advantages of direct-detection systems are enhanced resolution, lower overall costs due to fewer fabrication steps, and thinner packaging. The concept of the present invention, which relates to apparatus and methods for detecting the beginning and ending of an X-ray stream, is applicable to both the direct and indirect detection systems.

Both direct and indirect detection methods are available in two types of systems, integrated and free-standing systems. Integrated systems consist of the entire imaging system plus an X-ray source. By comparison, free-standing systems include only the imaging system; the user provides the X-ray source. In the integrated systems, the timing of the X-rays can be easily accomplished within the context of the entire system. However, in free-standing systems, the X-ray source is not hard-wired to the imaging system. In such systems, the X-ray source and the detection system are asynchronous to the extent that the detection system does not know in advance when the X-ray generator is about to turn on or off. This information is important primarily due to the nature of CCDs which typically must be run at all times, except during the critical integration time when the X-rays are being received and the image stored.

The signals stored by the CCDs are of two types. First, there is self-generated noise data, commonly referred to as "dark current" or fixed-pattern noise, which collects in the CCDs at a generally constant rate. This dark current results from environmental considerations such as temperature. The second type of data stored is image data emanating from the X-rays. In order to provide the highest signal-to-noise ratio, it is desirable to maximize the image data and minimize the noise data. This can be accomplished by "clocking off" the CCD detectors at all times except when the image rays are present. Then, when the image rays first arrive, the clocking can be stopped in order to collect the image data in the CCDs. By clocking the CCDs at all times outside of the integration period, the dark current or self-generated noise which is mixed with the image data is limited to that which is collected only during the integration time. This significantly raises the signal-to-noise ratio of the integrated data. The detection of both the onset of the X-rays as well as the cessation of the X-rays is critical to this process.

In the past, detection of these two events has been accomplished with the use of small, separate and distinct scintillation screens and associated diodes. In one construction, the diodes and scintillation screens have been enclosed in an opaque box so that they have been isolated from visible light. This box has been disposed in the path of the X-rays along with the CCD. In the manner previously disclosed, the scintillation screens have responded to the onset of X-ray images. Unfortunately, this construction has not been intrinsically radiation hard. In other words, X-ray exposure has tended to degrade the diodes and associated electronics so that their performance over time has diminished. Furthermore, in an environment where the size and particularly the thickness of the CCD head is important, this construction using scintillation screens and diodes has demanded as much as 60% of the total thickness of the CCD head.

SUMMARY OF THE INVENTION

The concept of the present invention overcomes these deficiencies of the prior art by providing at least one event detector which is separate from the image array. The event detector may include two CCD event arrays disposed in a transverse relationship to each other and mounted on a common substrate with the image array. These event arrays are disposed in the path of the X-rays along with the imaging array. When the X-rays strike the event arrays, their respective outputs can be combined to produce a substantial event signal which can then be relied on to herald both the onset and cessation of the X-ray stream. This signal can be used to stop the clocking of the image array immediately following the onset of the X-rays, and also to start the clocking immediately after cessation of the X-rays. The data developed between these two events, which substantially define the integration period, benefits from the high signal-to-noise ratio previously discussed.

Fabricating the event arrays into the same silicon substrate as the image array and using the same process steps, minimizes development costs and production costs. It also reduces the electronics necessary to process the event signal, and facilitates use of a single horizontal clock to drive both the image array and the event arrays.

A shared sense node can be provided at the output of the two event arrays to enhance the event signal. The reset timing of this sense node can be delayed so that many charge packets are integrated in a single event signal. This effectively increases the area over which charge is combined thereby enhancing the event signal and making accurate event detection much more efficient.

In one aspect of the invention, apparatus is adapted to visualize a scene in the form of image rays projecting along a path, and to display the scene on a cathode ray tube. The apparatus comprises a plurality of charge coupled device detectors disposed along the path to receive the image rays of the scene, the detectors being collectively arranged in an image array having properties for accumulating data. This data includes noise data, representative of environmental conditions, which accumulates in the detectors at a generally constant rate, as well as image data representative of the image rays of the scene, which accumulates in the detectors when the image rays are present along the path. A clock is provided for facilitating discharge of the data from the image array, the clock having a first state wherein the data is retained in the detectors and a second state wherein the data is discharged from the detectors. An event detector responsive to the presence of the image rays along the path places the clock in the first state when the image rays are present along the path, and places the clock in the second state when the image rays are absent from the path. In this manner, the noise data which combines with the image data in the detectors is limited to that which accumulates while the image rays are present along the path.

A further aspect of the invention includes a method for visualizing a scene in the form of image rays extending along the path, and for displaying the scene on a cathode ray tube. The method includes the steps of providing a first plurality of charge coupled device detectors in the form of an image array having properties for accumulating data. This data includes noise data which accumulates in the first detectors at a generally constant rate, and image data which accumulates in the first detectors when the image rays are present along the path. The method also includes the step of positioning the image array along the path, and providing a data clock having a first state permitting the data to be retained in the image detectors and a second state permitting the data to be discharged from the detectors. Setting the clock to the second state prior to the presence of the image rays in the path discharges the noise data from the image array. Providing a second plurality of charge coupled device detectors in the form of at least one event array facilitates detection of the presence and absence of the image rays in the path. Positioning this event array in the path also exposes the event array to the image rays. The clock is set to the first state when the event arrays detect the presence of the image rays, and is set to the second state when the event array detects the absence of image rays. Collecting the data from the image array that accumulated when the clock was in the first state forms an output signal which can be processed and introduced to the cathode ray tube to display the scene.

The resulting event detection is relatively fast as it enables adequate signal levels to be generated in only a few hundred microseconds. The event detector is sensitive due to the summing of the individual detectors by way of a delayed reset, and by summing the signals from more than one event array. The event detector is compact in providing the two event arrays around the periphery of the main imaging array thereby adding only a few microns of space. This event detection is as reliable as the elements forming the imaging array since they are fabricated in accordance with the same process. This similar fabrication of the event detectors also offers an insignificant cost impact to the overall system. The event arrays are spacially distributed insuring that adequate X-ray signal contacts at least one of the event arrays, and closely spaced to the imaging array insuring that the same image rays strike both the image array and the event arrays.

These and other features and advantages of the invention will be more apparent with a discussion of preferred embodiments and reference to the associated drawings.

DESCRIPTION OF PREFERRED EMBODIMENTS

Figure 1:
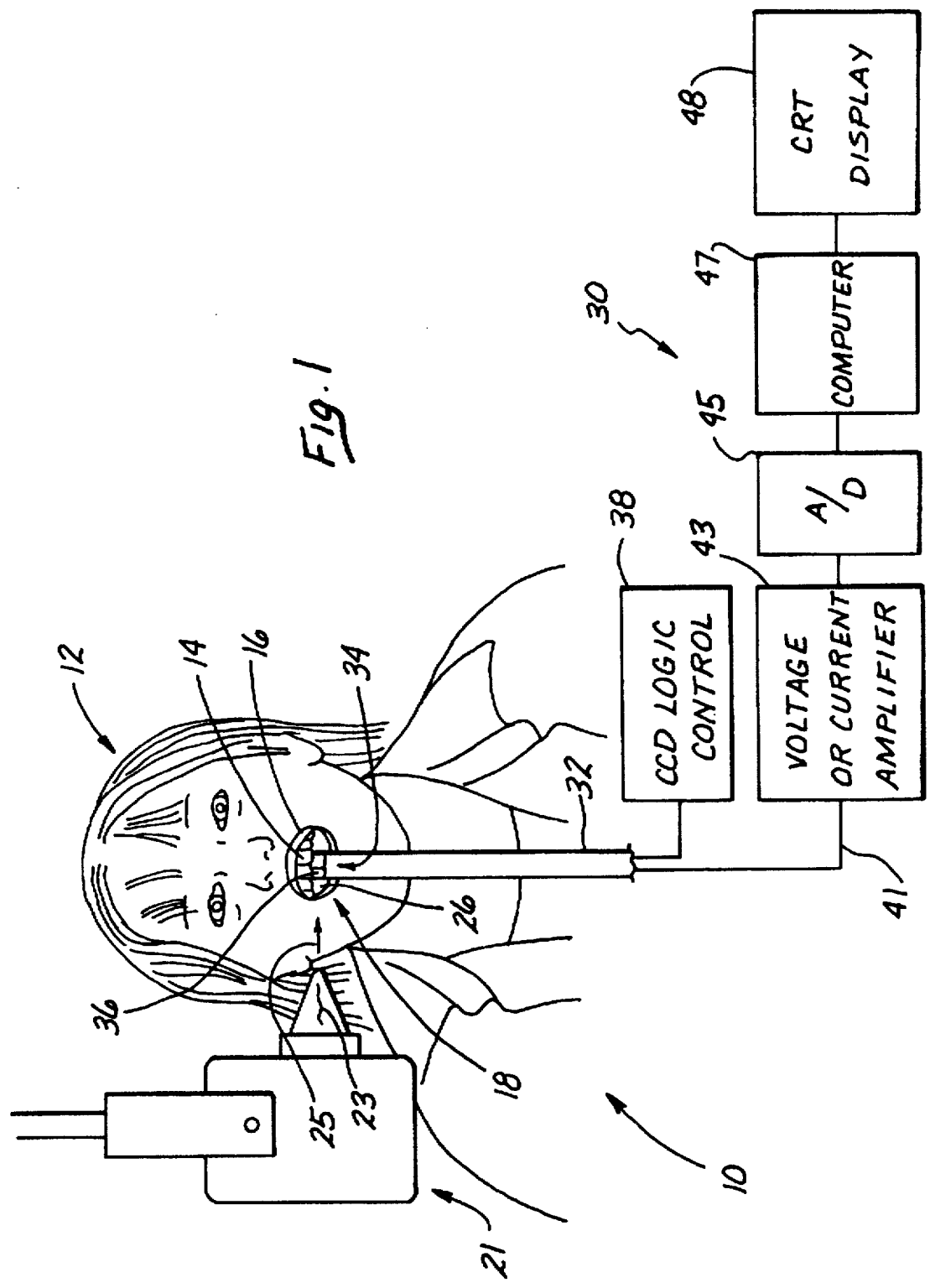
FIG. 1 is a perspective view of a dental patient and a block diagram view of an imaging system of the present invention.

A solid-state video X-ray imaging system is illustrated in FIG. 1 and designated generally by the reference numeral 10. The system 10 is illustrated in reference to a dental patient 12 having teeth 14 and gums 16 disposed in his mouth 18. The imaging system 10 includes an X-ray source 21 suitable for generating X-rays 23 and transmitting those X-rays along a path 25. The teeth 14 and gums 16, which are representative generally of any scene 22 are positioned along this path 25 and absorb the X-rays depending on the density of material in the path. On the opposite side of the teeth 14 and gums 16, the X-rays 23 are in the form of an image representative of the shape, density and other characteristics of the teeth 14 and gums 16. These X-rays on the opposite side of the scene 22 are referred to herein as image rays 26.

The image, represented by the image rays 26, is detected in a free-standing imaging detector 30 of the present invention. The image detector 30 includes a wand 32 having a detector head 34 which is disposed in the mouth 18 and suitably positioned along the path 25 to receive the image rays 26. A charge coupled device (CCD) detector array 36 is included on the detector head 34 and referred to in greater detail below as the image array 36. This image array 36 is controlled by CCD control logic 38 and provides a charge signal on a conductor 41. In a preferred embodiment the charge signal is enhanced by a voltage or current amplifier 43 which produces a video signal. This video signal can be converted in an A/D converter 45 and stored in a computer 47 for formatting to computer video and display on a CRT 48.

Figure 2:
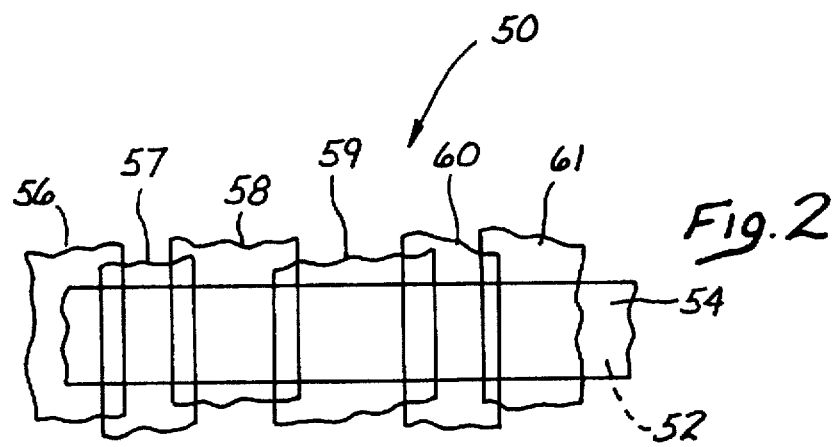
FIG. 2 is a top plan schematic view of a three-phase buried-channel providing for the controlled sweeping of electrons through a P-type silicon substrate.

Operation of the CCD detector array 36 is of particular interest to the present invention. CCD imaging arrays of this type are discussed in significant detail in an article entitled "Custom Photo Detector Arrays Meet Design Challenges", authored by one of the inventor, Paul Suni, and published in the April, 1994 issue of *Laser Focus World*. This article, which is incorporated herein by reference, discusses a three-phase buried-channel CCD similar to that illustrated in FIGS. 2 and 3.

Figure 3:
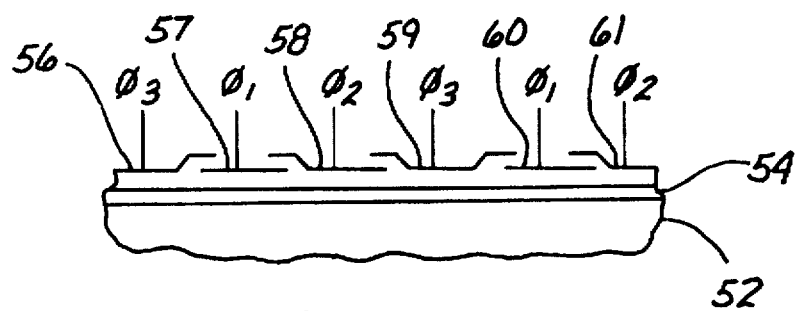
FIG. 3 is a side elevation view of the CCD illustrated in FIG. 2.

In these figures, a shift register 50 is shown in a top plan view (FIG. 2) and in an associated side elevation view (FIG. 3). The shift register 50 includes a P-silicon substrate 52 on which is deposited an N-type buried channel 54 along with a series of overlapping gate electrodes designated with the consecutive numerals 56–61. In the shift register 50 each group of three electrodes 56–61 is associated with an individual detector or charge well, and a pixel 70 (FIG. 4) which has a known location within the array 36 of detectors. When a photon, such as an X-ray photon, strikes a pixel 70, an electrical charge in the form of electrons, is stored in the associated charge packet. The greater the number of photons impinging on the pixel 70, the higher the charge of the packet. These charge packets can be moved over long distances along the CCD detector array 36 with little degradation of the charge. Accordingly, each of the pixels 70 stores a packet having a charge dependent upon the light intensity at an associated point in the scene 22, as represented by the image rays 26.

The information contained in the magnitude of the charge and the location of the pixel 70 is "clocked" from the image array 36 for example by a three-phase clock which sequentially moves the charge packets out of the array 36. Thus the charge packets are transferred along the array 36 by clocking the gate electrodes, 56–61 sequentially as shown by the clock phases $\phi_1$, $\phi_2$, and $\phi_3$ in FIG. 3.

Figure 4:
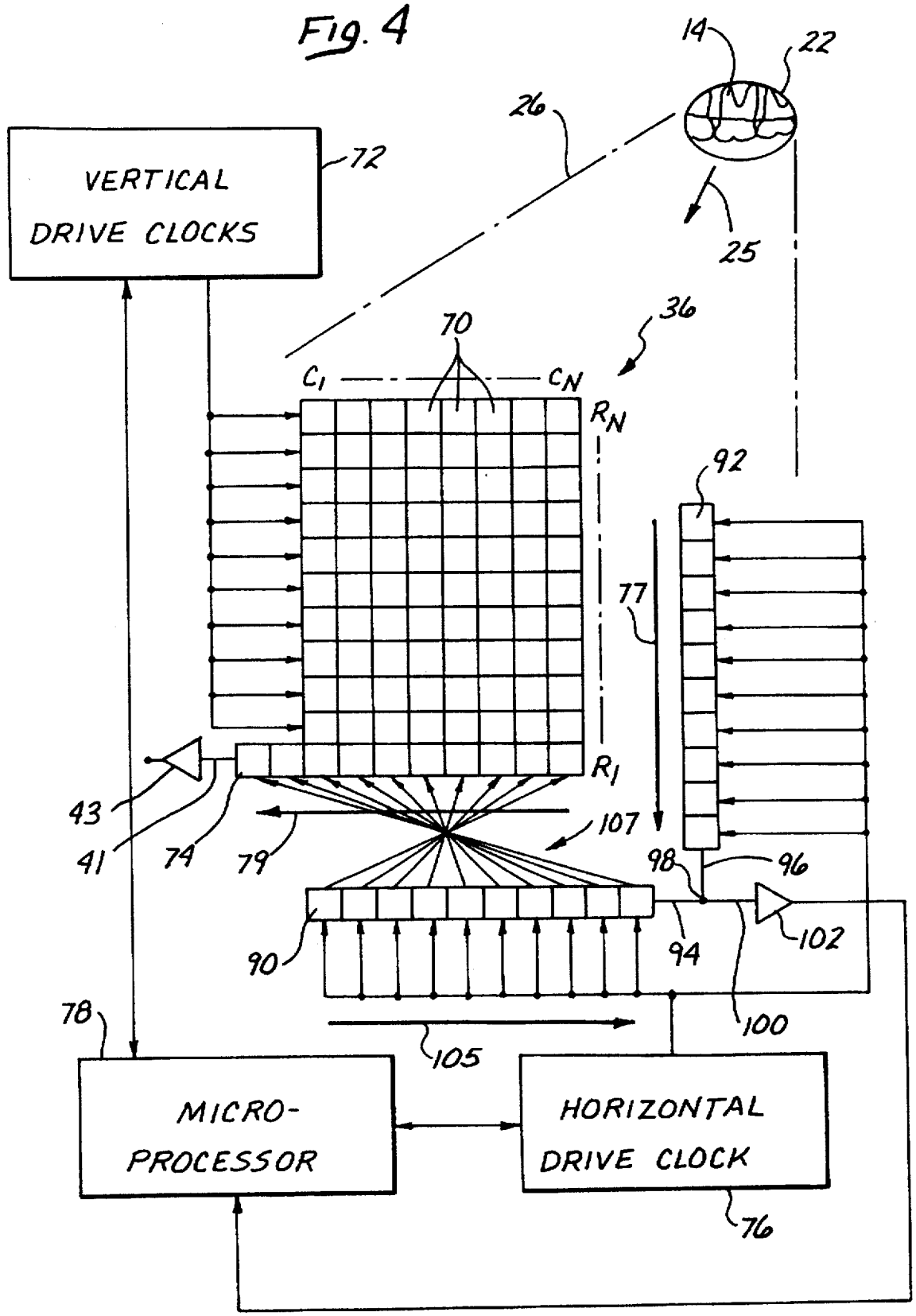
FIG. 4 is schematic view of an image array and two event arrays operable in accordance with the present invention.

This clocking of the array 36 can be better understood with reference to FIG. 4 wherein the CCD detectors forming the array 36 are each disposed in an associated one of the pixels 70 which are arranged in parallel rows $R_1$–$R_n$ and columns $C_1$–$C_n$.

As the image rays 26 are directed along the path 25, the pixels 70, each associated with a known location of the scene 22, store charge which is dependent upon the photon intensity at that point in the scene 22. This information in the charge packets is clocked from the pixel 70 using vertical drive clocks 72 which moves the rows $R_1$–$R_n$ of pixel information downwardly, consecutively and in parallel into a horizontal register 74. This downward movement of the rows $R_1$–$R_2$ is illustrated by an arrow 77 in FIG. 4.

As each row, such as the row $R_1$, occupies the horizontal register 74, a horizontal drive clock 76 clocks the individual pixel information serially out of the horizontal register 74 to form the charge signal in the conductor 41. Reconstructing this serial information into similar rows and columns reproduces the scene 22 in the recorder 47 and on the CRT 45. Operation of the clocks 72 and 76 is controlled in a preferred embodiment by a microprocessor 78. In the illustrated embodiment, the horizontal register 74 is clocked right to left as illustrated by an arrow 79.

As noted, the image rays 26 impinging on the image array 36 provide the charge packets in each of the pixels 70 with a charge having a magnitude depending on the intensity of the rays 26 at the respective pixel 70. The resulting charge in the packet can be referred to as image data. If this were the only data represented in the charge packet, the output signal would have a high degree of resolution; but this is not the case.

In addition to the image data, each charge packet also carries charge that results from the inherent noise present in an array of CCDs. This charge, which has no relationship to the image data, constitutes noise and is commonly referred to as "dark current" or fixed pattern noise. This noise results from various characteristics of the environment, such as temperature as well as the inherent characteristics of the image array such as pixel size, silicon purity, amplifier glow and various other design considerations. By comparison with the image data, which collects in the array 36 only when the image rays 26 are present, the noise data or dark current collects at a generally constant rate at all times. In other words, this noise data builds over time within each charge packet regardless of the presence or absence of the image rays 26.

In order to maximize the detection of the image data, it is necessary to increase the signal-to-noise ratio, or the ratio of image data to noise data to the greatest extent possible. This can be achieved in one aspect of the invention by insuring that each of the charge packets is "zeroed" at the time when image data starts to collect, and again after the image rays 26 stop and the image data ceases to collect. This develops a collection period, commonly referred to as the integration period, where the signal-to-noise ratio or the ratio of image data to noise data can be maximized.

In order to "zero" the charge packets associated with each pixel 70, both the vertical and horizontal clocks 72 and 76, respectively, can be operated to discharge the dark current or noise data from the image array 36. This happens on a continual basis as previously discussed where the vertical clock 72 moves the pixel rows $R_1$–$R_n$ sequentially in parallel into the horizontal register 74 (as shown by the arrow 77), and the horizontal clock 76 moves the charge packets sequentially in series along the horizontal register 74 (as shown by the arrow 79). In this manner, the continual operation of the clocks 72, 76 insures that the noise data does not collect to any appreciable level in the image array 36. It is evident that an electronic exposure control structure, such as is commonly used in CCD's, could also be used to purge the CCD from dark accumulated noise. With this approach, continuous clocking would not be necessary.

When the presence of the image rays 26 is detected, the CCD control logic 38 (FIG. 1), freezes the vertical clock 72 in order to immediately stop the clocking of the data. This frozen state is maintained during the entire integration period as the image data is collected. Of course, the dark current or noise data is also collected during the integration period. However, that noise data is limited to the noise charges that collected only during the integration period and the clock off period. In other words, noise data which collected prior to the clock off period and noise data which collects after the integration period, is not present in the charge packets which carry the image data.

The method and apparatus for establishing this window of time, the integration period, is of particular importance to the present invention. This is the case since the more accurately the window is defined the higher is the signal-to-noise ratio achieved with the present invention.

In a free-standing imaging system, there is no hard wire connection between the source of X-rays 21 and the detector 30. In such a system, one must sense the presence and absence of the image rays 26 at the detector 30 in order to develop event signals which can then be used to accurately frame the integration period. This detection of the presence of the image rays 26 must be fast, sensitive, compact, reliable and cost effective.

Figure 5:
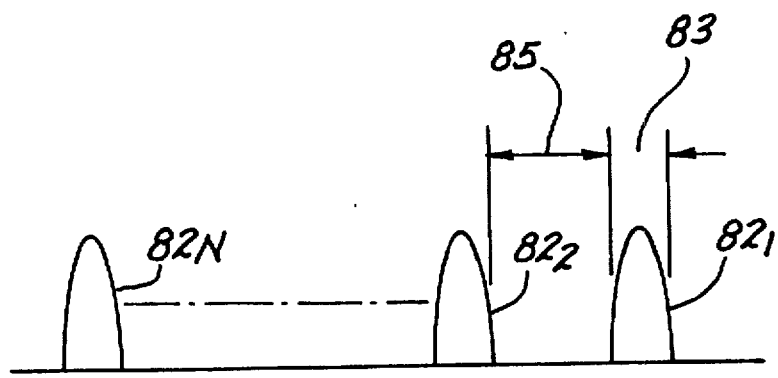
FIG. 5 is a time-result picture of the intensity of X-rays impinging on the rays illustrated in FIG. 4.

A typical X-ray signal is illustrated in FIG. 5 which shows a time-resolved picture of the X-ray intensity. Dental X-ray systems are typically pulsed devices which are half-wave rectified by the natural diode action of the X-ray tube (not shown). These pulses occur at a 60 Hz rate. Since the AC line voltage in the X-ray source 21 (FIG. 1) is stepped up in a simple transformer (not shown) to the operating potential of the X-ray tube (not shown), the anode-to-cathode output voltage varies over time in a half-sine manner. The resulting X-ray intensity is approximately described by a sine-squared function. The resulting X-ray signal 23, illustrated in FIG. 5, is composed of a 60 Hz train of pulses $82_1, 82_2 \ldots 82_n$. In this case, the pulses 82 have a pulse width such as five milliseconds, as shown at 83, and a pulse "dead space" such as twelve milliseconds, as shown at 85.

The typical exposure duration for a CCD-based imaging system might be on the order of 200 milliseconds to 625 milliseconds, corresponding to a train of the individual pulses 82 ranging from 12 to 38 in number. The actual exposure duration is dependent upon the operating voltage and current of the X-ray source 21, as well as the distance from the source 21 to the detector head 34. These parameters are generally set by the doctor, dentist or X-ray technician who chooses an appropriate number of pulses in the train.

In order to accurately frame the integration period, it is necessary to detect the leading edge of the first pulse $82_1$ in the train within a time period of one to two milliseconds. Detecting the leading edge of the first pulse $82_1$ within this time frame enables one to freeze the vertical clock 72, officially beginning the integration period. A one millisecond delay in detection of the first pulse $82_1$ at the beginning of a 12-count pulse train, would insure that 98% of the incident X-ray photons would arrive within the integration period. This percentage rises with an increase of the pulse count above twelve.

The detection of the leading edge of the first pulse $81_1$ is accomplished in a preferred embodiment with the addition of at least one, and preferably two CCD event detectors or arrays 90 and 92. These event arrays 90, 92 are similar to the image array 36 in that they are also sensitive to the image rays 26 from the scene 22 and accordingly develop charge packets containing data. Detection of this data from the event arrays 90, 92 does not result in reconstruction of the image as was the case of the image array 36. Rather, detection of the data in the event arrays merely indicates the timing of two events, namely the time when the image rays 26 are present in the path, and the time when the image rays 26 are absent from the path 25.

Of course it is important that the event arrays, 90, 92 be positionable along the path 25 so that the presence or absence of the image rays 26 can be detected. In a preferred embodiment, these event arrays 90, 92 are positioned on the detection head 34 along with the image array 36. The positioning and operation of the event arrays 90, 92 can be independent of the image arrays 36. However, there are cost and reliability synergies which are achieved in a preferred embodiment wherein the event arrays 90, 92 are closely spaced to the image array 36.

In a preferred embodiment, the event arrays are actually formed on the same silicon substrate 52 (FIG. 3). For example, the event array 90 can be formed as an additional row of the CCD detectors, and the event array 92 can be formed as an additional column of the CCD detectors. With the close spacing of the event arrays 90, 92 relative to the image array 36, the image rays 26 which impinge upon the array 36 are most likely to also impinge on the event arrays 90, 92. In a preferred embodiment, this spacing between the image array 36 and the event arrays 90, 92 is approximately 10 to 1000 microns.

The relative disposition of the two event arrays 90, 92 can also be important as one contemplates the nature of the scene 22. Particularly in the case of dental X-rays, a vertical array, such as the event array 92 would typically be exposed to a low energy portion of the scene 22 representative of the teeth 14. This low energy area of the scene would develop fewer charges within the event array 92 then would be the case with an array, such as the event array 90 which is formed transverse (such as horizontal) relative to the vertical array 92. Rather than placing this second array 90 parallel to the array 92 where it is apt to receive the same low signal level, the transverse orientation of the array 90 increases the likelihood that a different signal will develop, for example, at the horizontal position of the low density gums 16.

In a manner similar to that discussed with reference to the horizontal register 74, the event arrays 90 and 92 can be serially clocked by the horizontal clock 76 into respective output lines 94 and 96 which in a preferred embodiment, are joined at a common sense node 98. This sense node 98 simultaneously collects the event data from both of the arrays 90, 92, and provides an event signal on a conductor 100. This event signal can be enhanced in an amplifier 102 and introduced to the microprocessor 78 which controls the clocks 72, 76.

The three-phase horizontal clock 76 which drives the event arrays 90, 92 sequentially moves the charge from one end of the array to the other. In the illustrated embodiment, this sequential movement is left-to-right as evidenced by an arrow 105 for the event array 90. The sequential movement of charge in the event array 92 is top-to-bottom as shown by the arrow 77.

As previously noted, the sequential charge movement in the horizontal register 74 is right-to-left as shown by the arrow 78, so the drives of the horizontal clock 76 must be switched end-for-end relative to the event array 90 as shown by the crossed arrows 107.

Although the clock drive for the event arrays 90, 92 can be slaved to that of the horizontal register 74 of the image array 36, their reset gate timings may differ. In a preferred embodiment the reset gate signal "clears" the sense node 98 prior to the charge being measured by the output amplifier 102. By comparison, the horizontal register 74 of the image array 36 is reset on a pixel-by-pixel basis. This difference in the reset gating of the event array 90, 92 is preferred in order to insure that many charge packets are summed at the sense node 98. This strengthens the event signal on conductor 100.

While this delayed reset lengthens the interval between successive sense operations, it provides the advantage of making the effective event detection area larger by combining charge from many individual detectors. A larger effective detection area increases the event signal level making accurate event detection much easier. In a preferred embodiment, the charge from a few tens of individual detectors is collected prior to reset. This enables reset timing to occur every few hundred microseconds which still permits both event arrays 90, 92 to be summed and measured in about one millisecond. The final selection of the number of summed detectors, and hence the time duration between sense node resets, is dependent upon the quantum efficiency of the detectors, the overall system noise, and the minimum permissible sense bandwidth.

Figure 6:
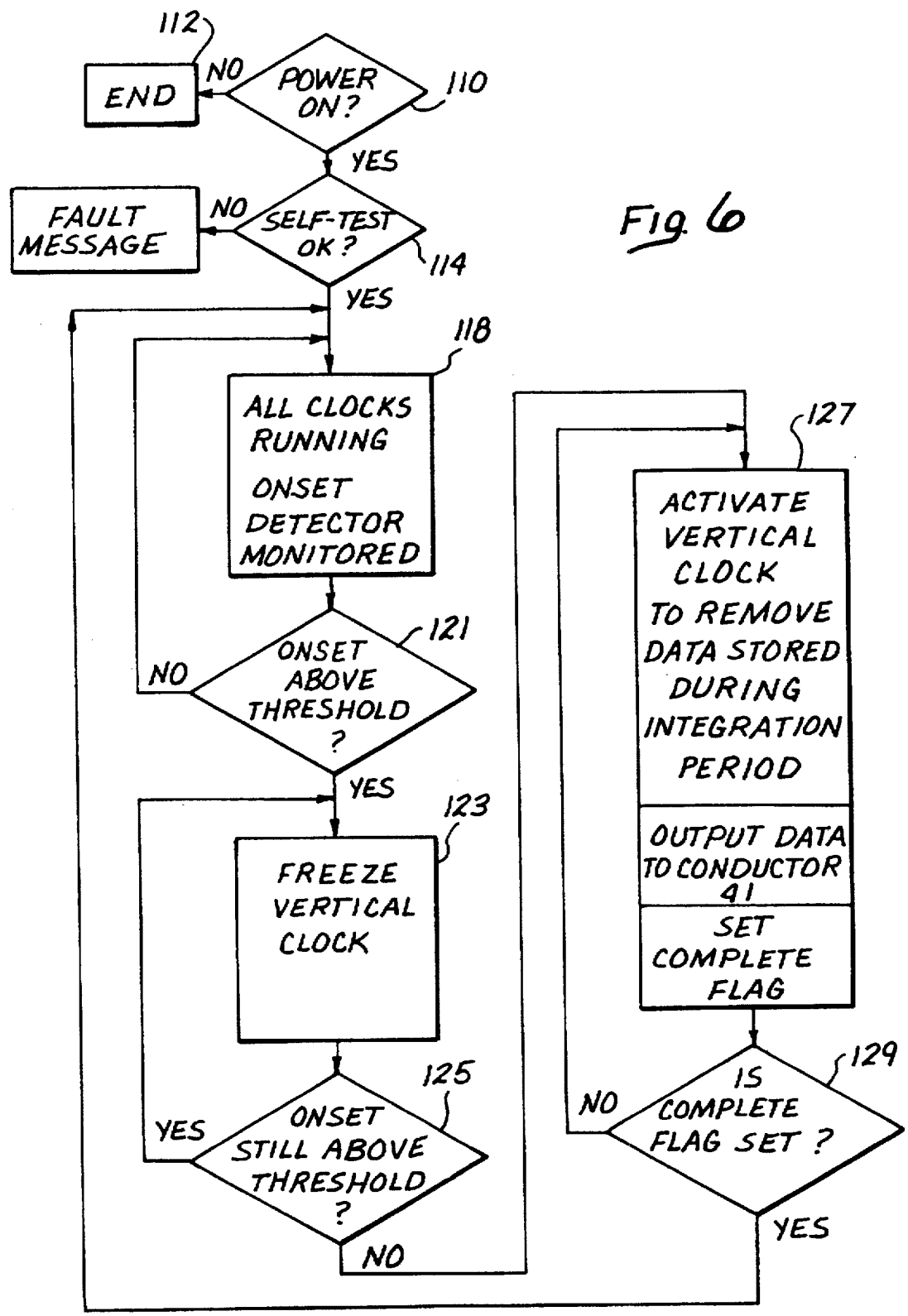
FIG. 6 is logic diagram associated with a method for detecting the onset and cessation of X-rays along the path.

Operation of the detector 30 in a preferred method of the invention can be best understood with reference to the logic chart of FIG. 6. In this logic diagram various questions are addressed and set forth in diamond shaped boxes, and various actions are called for and set forth in rectangular-shaped boxes. In the following discussion, these boxes are referred to as merely as diamonds or rectangles.

Initially the system queries in a diamond 110 as to whether the power is on. If not, the program is ended as shown by the rectangle 112. If the power is on, a self-test can be conducted as shown by the diamond 114. If a fault occurs, a message is given in the rectangular box 116. If the self-test is passed, the rectangle 118 insures that all clocks are running and that the event detectors 90, 92 are being monitored.

At this point, the logic queries in the diamond 121 whether the event signal on the conductor 100 is above a certain threshold. Such a signal would indicate that image rays 26 are impinging on at least one of the event arrays 90, 92. If the event signal is not above threshold, the clocks 72, 76 continue to run and the sense node 98 continues to be monitored in accordance to rectangle 118.

If the event signal is above threshold, the vertical clock 72 is frozen in accordance with the rectangle 123. This starts the integration period during which the sense node 98 is monitored to determine if the event signal is still above threshold. If this question in a diamond 125 is true, the vertical clock 72 continues to be frozen as specified in the rectangle 123. However, once the event signal falls below threshold, the answer to the logic question in diamond 125 is false. This heralds the end of the integration period. At this point the vertical drive clock 72 is activated and data stored during the integration period is clocked from the array 36 in accordance with the rectangle 127.

When all of the image data has been removed, a "complete" flag is set. This setting of the complete flag is monitored in a diamond 129. Once the complete flag is indicated to be set, the logic returns to rectangle 118 where all clocks are running and the sense node 98 is again monitored for an event signal.

The resulting detector 30 and preferred method of operation illustrated in FIG. 6, meet the criteria initially set forth for event detection. More specifically, the event detector 30 is relatively fast since the event signal level can be generated in less than a few hundred microseconds. Sensitivity of the detector 30 is enhanced by delaying the reset of event detectors 90, 92 and thereby summing many individual detector elements. The event signal is further enhanced by summing the signals from the two separate event arrays 90 and 92 in the sense node 98. This facilitates error signal levels as high as on the order of volts with background noise measured in less than tens of millivolts. The detector 30 is relatively compact with the two event detectors 90, 92 being formed around the periphery of the image array 36 adding less than a millimeter space to the array chip on the detector head 34.

The various aspects of this invention have been described with reference to preferred embodiments and methods which are specifically adapted to dental X-rays. It will be appreciated that the invention is equally applicable to other environments where the scene 22 may be represented in image rays other than the image X-rays 26. Sensitivity to other frequencies from the infrared to ultraviolet spectrums can be accomplished with other types of CCD detector arrays. Similarly, the event arrays 90 and 92 can be replaced with any means for monitoring the presence of the image rays along the path 25. Constructing these detectors with the same CCD technology as the image array 36 can offer advantages of cost savings and space utilization.

The event arrays 90 and 92 can be provided with any orientation in proximity to the image array 36. While the perpendicular orientation of the array 90 relative to the array 92 is particularly adapted to the disclosed embodiment, any generally transverse orientation could achieve a similar result. Furthermore, the data collected in the horizontal register 74 as well as the event arrays 90, 92 can be clocked in any direction suitable to a particular configuration of the arrays 36, 90 and 92 on the substrate 52.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. Apparatus adapted to visualize a scene in the form of image rays projecting along a path, and to display the scene on an image display device, comprising:

a plurality of charge coupled device detectors disposed along the path to receive the image rays of the scene, the detectors being collectively arranged in an image array having properties for accumulating data;

the data including noise data and image data, the noise data being representative of environmental conditions and accumulating in the detectors at a generally constant rate, the image data being representative of the image rays of the scene which accumulates in the detectors when the image rays are present along the path;

a clock for facilitating discharge of the data from the image array, the clock having a first state wherein the data is retained in the detectors of the image array and a second state wherein the data is discharged from the detectors of the image array;

an event detector responsive to the presence of image rays along the path to place the clock in the first state during an integration period when the image rays are present along the path and to place the clock in the second state when the image rays are absent from the path; whereby the noise data which combines with the image data in the image detectors is limited to that which accumulates during the integration period while the image rays are present along the path.

2. The apparatus recited in claim 1 wherein the event detector comprises at least one event charge coupled device detector.

3. The apparatus recited in claim 2 wherein the image array is formed on a silicon substrate and the event detector is formed on the same silicon substrate with the image array.

4. The apparatus recited in claim 3 wherein the at least one event charge coupled device detector includes:

a first event array extending in a first direction; and a second event array extending in a second direction transverse to the first direction.

5. The apparatus recited in claim 4 wherein:

the charge coupled device detectors of the image array are disposed in rows extending in a third direction and columns extending in a fourth direction;

the first direction is generally parallel to the third direction;

the second direction is generally parallel to the fourth direction; and the third direction is generally perpendicular to the fourth direction.

6. The apparatus recited in claim 2 further comprising an output register, and the clock includes:

a first clock coupled to the image array for moving the data in parallel into the output register;

a second clock coupled to the output register for discharging the data in series from the output register; and means for coupling the clock to the at least one event detector for discharging the at least one event detector.

7. The apparatus recited in claim 1 wherein the image rays are X-rays.

8. A method for visualizing a scene in the form of image rays extending along a path, and for displaying the scene on an image display cathode ray tube, comprising the steps of:

providing a first plurality of charge couple device detectors in the form of an image array having properties for accumulating data, the data including noise data which accumulates in the first detectors at a generally constant rate and image data which accumulates in the first detectors when the image rays are present along the path;

positioning the image array along the path to permit the image rays to impinge on the image array;

providing a data clock having a first state permitting the data to be retained in the image array, and a second state permitting the data to be discharged from the image array;

setting the clock to the second state, prior to the presence of image rays in the path, in order to discharge the noise data from the image array;

providing a second plurality of charge couple device detectors in the form of at least one event array having properties for detecting the presence and absence of image rays in the path;

positioning the at least one event array in the path;

setting the clock to the first state when the event array detects the presence of image rays in the path;

setting the clock to the second state when the event array detects the absence of image rays in the path;

collecting from the image array the data accumulated when the clock was in the first state to form an output signal; and introducing the output signal to a cathode ray tube to display the scene on the cathode ray tube.

9. The method recited in claim 8 wherein:

the step of providing the first detectors, include the step of providing the first detectors in the form of the image array wherein the detectors are arranged in a plurality of generally parallel rows and a plurality of generally parallel columns;

the step of providing a data clock includes the step of providing a first data clock for moving the data into successive rows and into an output register, and providing a second data clock for moving the data from the output register;

the setting step includes the step of setting the first clock; and the collecting step includes the step of operating the second clock to move the data from the output register in the form of the output signal.

10. The method recited in claim 8 wherein:

the providing a first plurality of charge coupled device detectors step includes the step of forming the image array on a substrate;

the providing a second plurality of charge coupled device detectors step includes the step of forming the at least one event array on the substrate with the image array; and the steps for positioning the image array and the at least one event array in the path occur substantially simultaneously.

11. The method recited in claim 10 wherein:

the step of providing the second plurality of charge coupled device detectors includes the steps of providing a first event array and providing a second event array;

the step of positioning the at least one event array includes the step of positioning the first event array on the substrate generally parallel to the rows of the image array; and positioning the second event array on the substrate generally parallel to the columns of the image array.

12. Apparatus adapted to visualize a scene in the form of image rays projecting along a path, and to display the scene on an image display device, comprising;

a plurality of charge coupled device detectors disposed along the path to receive the image rays of the scene, the detectors being collectively arranged in an image array having properties for accumulating data;

a clock facilitating discharge of the data from the image array, the clock having a first state wherein the data is retained in the detectors of the image array, and a second state wherein the data is discharged from the detectors of the image array; and an event detector responsive to the presence of the image rays along the path to place the clock in the first state when the image rays are present along the path and to place the clock in the second state when the image rays are absent from the path.

13. The apparatus recited in claim 12 wherein the event detector comprises at least one event charge coupled device detector.

14. The apparatus recited in claim 13 wherein the at least one event charge coupled device detector includes:

a first event array extending in a first direction; and a second event array extending in a second direction transverse to the first direction.

15. The apparatus recited in claim 14 wherein:

the charge coupled device detectors of the image array are disposed in rows extending in a third direction and columns extending in a fourth direction;

the first direction is generally parallel to the third direction;

the second direction is generally parallel to the fourth direction; and the third direction is generally perpendicular to the fourth direction.

16. The apparatus recited in claim 12 further comprising an output register, and the clock includes:

a first clock coupled to the image array for moving the data in parallel into the output register;

a second clock coupled to the output register for discharging the data in series from the output register; and means for coupling the second clock to the at least one event detector for discharging the at least one event detector.

* * * * *